United States Patent [19]

Seward et al.

[11] Patent Number: 5,345,940
[45] Date of Patent: Sep. 13, 1994

[54] TRANSVASCULAR ULTRASOUND HEMODYNAMIC AND INTERVENTIONAL CATHETER AND METHOD

[75] Inventors: James B. Seward; Abdul J. Tajik, both of Rochester, Minn.

[73] Assignee: Mayo Foundation for Medical Education and Research, Rochester, Minn.

[21] Appl. No.: 972,626

[22] Filed: Nov. 6, 1992

Related U.S. Application Data

[63] Continuation-in-part of Ser. No. 790,580, Nov. 8, 1991.

[51] Int. Cl.⁵ .................... A61B 8/00; A61B 17/32
[52] U.S. Cl. .................... 128/662.06; 606/159; 128/660.03
[58] Field of Search .................. 128/660.03, 661.09, 128/662.06

[56] References Cited

U.S. PATENT DOCUMENTS

| | | | |
|---|---|---|---|
| 4,162,282 | 7/1979 | Fulwyler et al. | 264/9 |
| 4,310,505 | 1/1982 | Baldeschwieler et al. | 424/1 |
| 4,533,254 | 8/1985 | Cook et al. | 366/176 |
| 4,582,067 | 4/1986 | Silverstein et al. | 128/662.06 |
| 4,586,512 | 5/1986 | Do-huu et al. | 128/660 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman | 514/6 |
| 4,689,986 | 9/1987 | Carson et al. | 73/19 |
| 4,728,575 | 3/1988 | Gamble et al. | 428/402.2 |
| 4,728,578 | 3/1988 | Higgins et al. | 428/462 |
| 4,737,323 | 4/1988 | Martin et al. | 264/4.3 |
| 4,781,871 | 11/1988 | West, III et al. | 264/4.3 |
| 4,794,931 | 1/1989 | Yock | 128/662.06 |
| 4,841,977 | 6/1989 | Griffith et al. | 128/660.03 |
| 4,865,836 | 9/1989 | Long, Jr. | 424/5 |
| 4,887,605 | 12/1989 | Angelsen et al. | 128/660.03 |
| 4,893,624 | 1/1990 | Lele | 128/399 |
| 4,900,540 | 2/1990 | Ryan et al. | 424/9 |
| 4,911,170 | 3/1990 | Thomas, III et al. | 128/662.06 |
| 4,921,706 | 4/1990 | Roberts et al. | 424/450 |
| 4,936,281 | 6/1990 | Stasz | 128/662.06 |
| 4,947,852 | 8/1990 | Nassi et al. | 128/662.06 |
| 4,951,677 | 8/1990 | Crowley et al. | 128/662.06 |
| 4,957,111 | 9/1990 | Millar | 128/662.06 |
| 5,002,059 | 3/1991 | Crowley et al. | 128/662.06 |
| 5,022,399 | 6/1991 | Biegeleisen | 128/662.06 |
| 5,038,789 | 8/1991 | Frazin | 128/662.06 |

FOREIGN PATENT DOCUMENTS

| | | |
|---|---|---|
| 0361894 | 4/1990 | European Pat. Off. . |
| WO80/02365 | 11/1980 | PCT Int'l Appl. . |
| WO82/01642 | 5/1982 | PCT Int'l Appl. . |
| WO86/01103 | 2/1986 | PCT Int'l Appl. . |

OTHER PUBLICATIONS

Cheng et al, *Investigative Radiology*, vol. 22, pp. 47–55 (1987).
Crowe et al., *Archives of Biochemistry and Biophysics*, vol. 242, pp. 240–247 (1985).
Crowe et al., *Archives of Biochemistry and Biophysics*, vol. 220, pp. 477–484 (1983).
Dorland's Illusrated Medical Dictionary, p. 946, 27th ed. (W. B. Saunders Company, Philadephia 1988).
Fukuda et al., *J. Am. Chem. Soc.*, vol. 108, pp. 2321–2327 (1986).
Hope et al., *Biochimica et Biophysica Acta*, vol. 812, pp. 55–65 (1985).

*Primary Examiner*—Francis Jaworski
*Attorney, Agent, or Firm*—Merchant, Gould, Smith, Edell, Welter & Schmidt

[57] ABSTRACT

A self contained ultrasound device for the delivery of therapeutic and other types of tools to be visualized in an ultrasound-type environment within the blood before, during, and after an intervention includes a catheter having a catheter body with a proximal and distal ends. The catheter contains an ultrasonic transducer proximate its distal end. An access port is provided in the catheter for delivery of a therapeutic device or the like to proximate the distal end of the catheter body. A guide wire port is further provided for insertion therethrough of a guide wire.

8 Claims, 6 Drawing Sheets

OTHER PUBLICATIONS

*Liposome Technology,* Gregoriadis, G., ed., vol. I, pp. 1–18, 29–35, 51–65 and 79–107 (CRC Press, Inc. Boca Raton, Fla. 1984).

Madden et al., *Chemistry and Physics of Lipids,* vol. 53, pp. 37–46 (1990).

Mayer et al., *Biochimica et Biophysica Acta,* vol. 858, pp. 161–168 (1986).

Mayhew et al., *Methods in Enzymology,* vol. 149, pp. 64–77 (1987).

Regen et al., *J. Am. Chem. Soc.,* vol. 102, pp. 6638–6640 (1980).

Sinkula et al., *J. Pharm. Sci.,* vol. 64, pp. 181–210 (1975).

Shiina et al., "Hyperthermiaby Low-frequency Synthesized Ultrasound", *IEEE Engineering,* pp. 879–880, vol. 2 (abstract).

McAvoy et al., *IEEE Engineering, Ultrasonics Symposium Proceedings,* vol. 2, pp. 677'1248 (abstract).

Pandian, N. G., et al.: Transvascular and Intracardiac Two-Dimensional High-Frequency Ultrasound Imaging of Pulmonary Artery and Its Branches in humans and Animals. (Exhibit D)

Masahito Moriuchi et al., "Transvenous Echocardiography: Experimental Feasibilty Study", *Japan J. Med. Ultrasonics,* 19:229–235 (1992).

Nishimura et al.: "Intravascular Ultrasound Imaging: In Vitro Validation and Pathologic Correlation", JACC, 16:145–154 (1990). (Exhibit F)

Pandian N. G. et al., "Intracardiac Echocardiography. Experimental Observations on Intracavitary Imaging of Cardiac Structures with 20-MHz Ultrasound Catheters", *Echocardiography,* vol. 8: 127–134 (1991). (Exhibit A)

Pandian et al., "Intracardiac, Intravascular, Two-Dimensional, High-Frequency Ultrasound Imaging of Pulmonary Artery and Its Branches in Humans and Aninmals", *Circulation,* 81:2007–2012 (1990).

Schwartz et al., "Intracardiac Echocardiographic Guidance and Monitoring During Aortic and Mitral Balloon Valvuloplasty: In Vivo Experimental Studies", Abstract *JACC,* 15:104A (Feb. 1990).

Schwartz et al. "Real-Time Intracardiac Two-Dimensional Echocardiography: An Experimental Study of In Vivo Feasibility, Imaging Planes, and Echocardiographic Anatomy", *Echocardiography,* 7:443–445 (1990).

Schwartz et al, "Intracardiac Echocardiography in Humans Using a Small-Sized (6F), Low Frequency (12.5 MHz) Ultrasound Catheter", *JACC,* 21:189–198 (Jan. 1993).

Seward et al., "Transvascular and Intracardiac Two-Dimensional Echocardiogrpahy", *Echocardiography,* 7:457–464 (1990).

Weintraub et al., "Realtime Intracardiac Two-Dimensional Echocardiography in the Catheterization Laboratory in Humans", Abstract, *JACC,* 15:16A (Feb. 1990).

"Cardiovascular Imaging Systems' Intracardiac Imaging Catheter", *M-D-D-I Reports,* publisher: F-D $\propto$ C Reports, Inc., pp. I&W-6 and I&W-7 (Mar. 30, 1992).

Copy of a MDDI Reports (Exhibit H), publisher: F-D-C Reports, Inc. dated Mar. 30, 1992, I&W6 and I&W7 (2 pages).

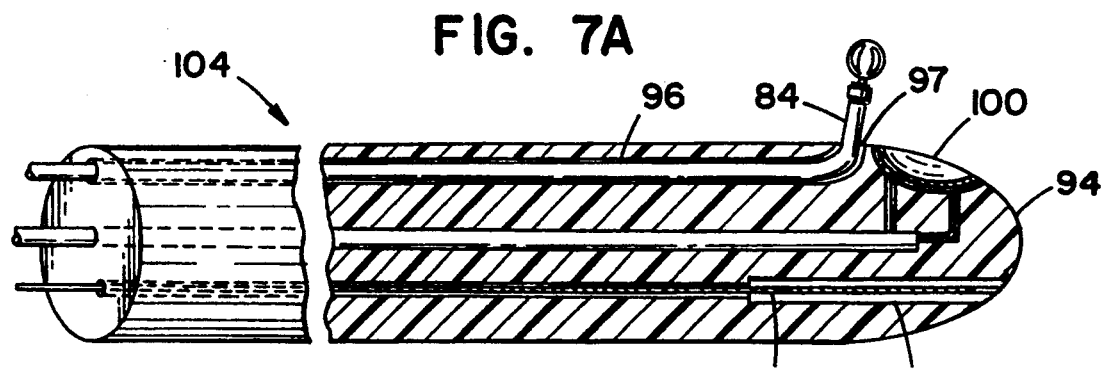
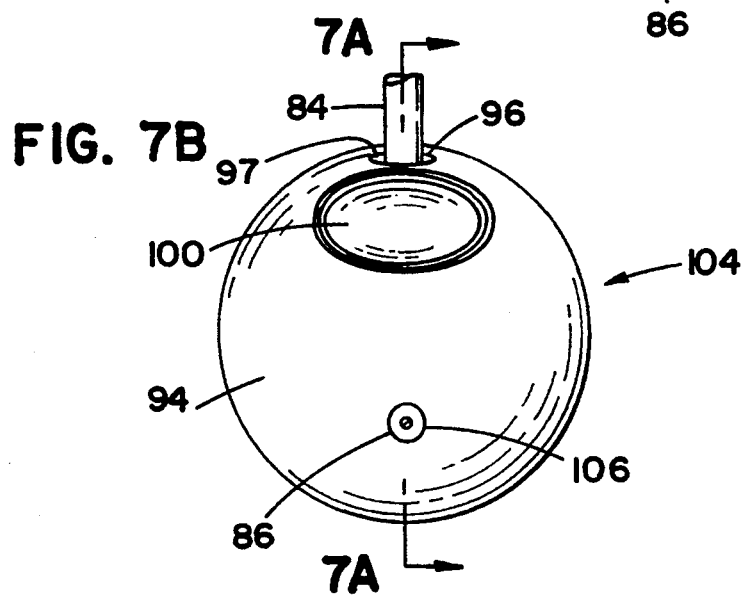
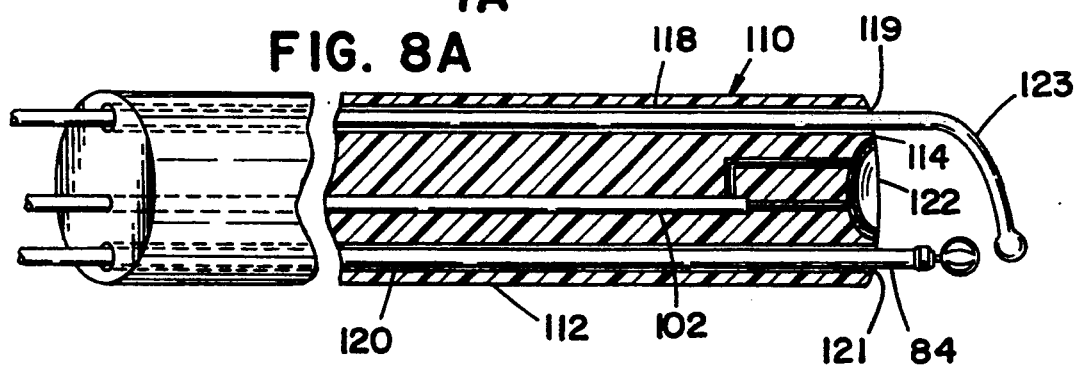
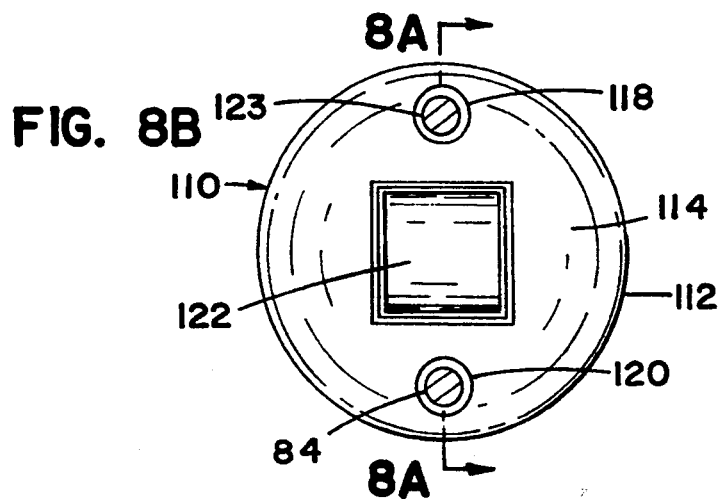

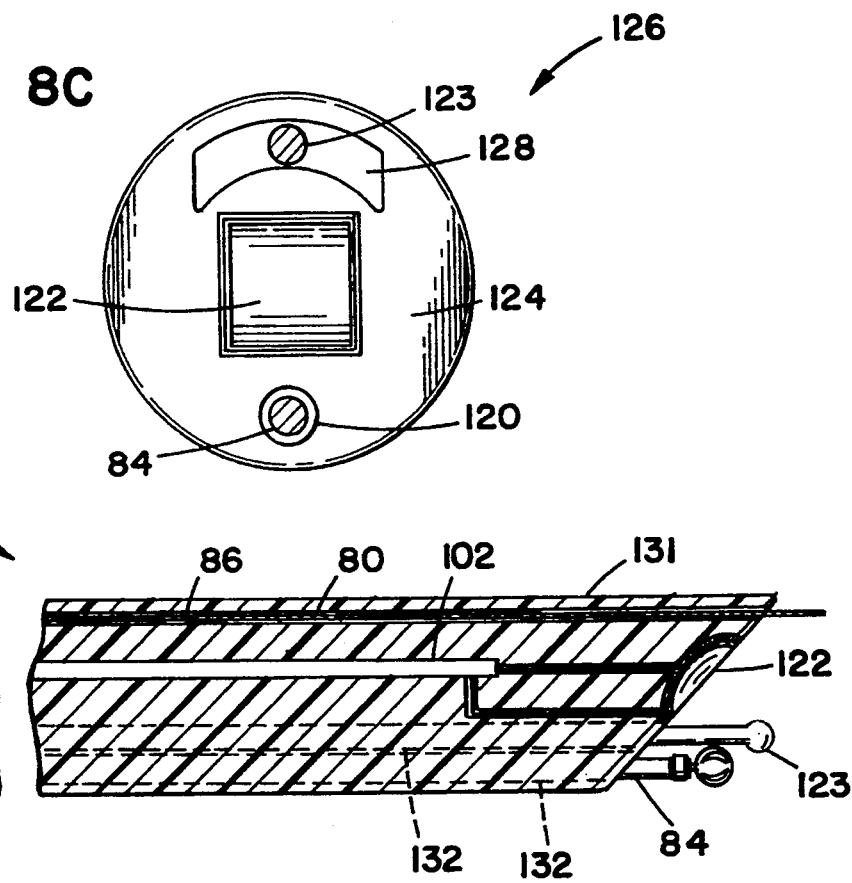
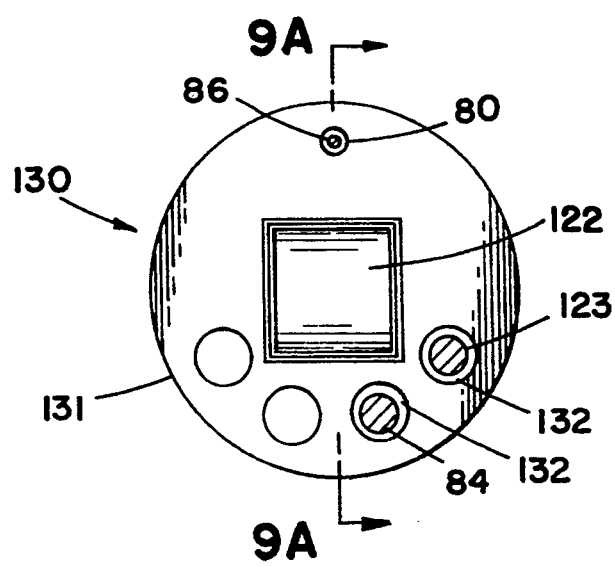

TRANSVASCULAR ULTRASOUND HEMODYNAMIC AND INTERVENTIONAL CATHETER AND METHOD

This application is a continuation-in-part application of U.S. application Ser. No. 07/790,580 filed on Nov. 8, 1991.

BACKGROUND OF THE INVENTION

The present invention relates to an ultrasonic and interventional catheter and method. More particularly, the present invention relates to such a catheter which provides imaging and hemodynamic capability. Further, the invention relates to such a catheter which provides transvascular and intracardiac imaging.

Current x-ray fluoroscopy can localize radio paque devices within the cardiovascular system and outline silhouetted anatomy. Precise localization of intracardiac anatomy is not possible; e.g., directing a catheter predictably and repetitively through the same precise point within the heart.

Ultrasound (echocardiography) can be utilized to image detailed cardiac, intracardiac, and vascular anatomy. Additionally, function, hemodynamics, and visualization of blood flow is possible. Doppler echocardiography, which utilizes the physics of ultrasound frequency to determine velocity and direction of blood flow, is used to determine pressure and flow and visualize blood movement within the cardiac chambers.

Ultrasound is increasingly utilized as a substitute for cardiac catheterization.

Currently, many interventional procedures can be performed through a catheter; e.g., balloon dilation and valvuloplasty and ablation of abnormal cardiac tissue are two frequently performed procedures.

Ultrasound has recently entered into invasive applications. Transesophageal echocardiography is the most widely utilized invasive ultrasound technique. Intravascular ultrasound utilizing miniature transducers mounted on a catheter are now undergoing vigorous clinical trials. Intracardiac imaging devices have received very limited investigation.

Increasingly, therapeutic cardiac catheterization is displacing diagnostic cardiac catheterization. Thus, there is an acceptance of catheter technology as a means of altering cardiac anatomy or conduction system. Balloon angioplasty, utilization of defect closure devices, and electrical interruption of anomalous conduction pathways are now considered accepted practice. However, most of these procedures are rather gross in nature; e.g. a large balloon splitting an obstructed valve, crude devices inserted into defects, and application of thermal or electric energy to interrupt the conduction system or produce defects in septa.

SUMMARY OF THE INVENTION

The present invention relates to an ultrasonic and interventional catheter. The present invention more particularly relates to an ultrasonic and interventional catheter which provides imaging and hemodynamics, blood pressure and flow, capability. Further, the invention relates to such a catheter which images through the vascular system, i.e., transvascular and intracardiac.

In one embodiment, the present invention relates to a catheter apparatus comprising an elongated flexible body having proximal and distal ends with an ultrasonic transducer mounted proximate the distal end of the catheter body to transmit ultrasound and receive resulting echoes so as to provide a field of view within which flow rates can be measured and features imaged. An electrical conductor is disposed within the catheter body for electrically connecting the transducer to control circuitry external of the catheter. A port means is disposed in the catheter body and extends from proximate the proximal end of the catheter body to proximate the distal end of the catheter body for receiving a therapeutic device whereby a therapeutic device can be delivered to proximate the distal end of the catheter for operation within the ultrasonic transducer field of view. A guide wire port means is further disposed in the catheter body and extends from proximate the proximal end of the catheter body to proximate the distal end of the catheter body for receiving a guide wire.

The present invention further relates to a medical system comprising a catheter, control circuitry means for controlling operation of an ultrasonic transducer disposed on the catheter and display means for displaying flow rates and features imaged by the ultrasonic transducer. In one embodiment of this invention, the catheter comprises an elongated flexible body having proximal and distal ends. The ultrasonic transducer is mounted proximate the distal end of the catheter body to transmit ultrasound and receive resultant echoes so as to provide a field of view within which flow rates can be measured and features imaged. An electrical conductor is disposed in the catheter body for electrically connecting the transducer to control circuitry external of the catheter. Port means is further disposed in the catheter body and extends from proximate the proximal end of the catheter body to proximate the distal end of the catheter body for receiving a therapeutic device whereby the therapeutic device can be delivered to proximate the distal end of the catheter for operation within the ultrasonic transducer field of view. A guide wire port means is further disposed in the catheter body and extends from proximate the proximal end of the catheter body to proximate the distal end of the catheter body for receiving a guide wire.

The present invention also relates to a method of therapeutic intervention in a living body. The method includes the steps of inserting a catheter into the body, the catheter having a body with proximal and distal ends. A surgical device is inserted into the body through a port disposed in the catheter body and extending from proximate the proximal end of the catheter body to the distal end of the catheter body. An ultrasonic transducer disposed proximate the proximal end of the catheter body is pulsed to transmit ultrasound and receive resultant echoes. The surgical device is operated within a field of view provided by the ultrasonic transducer. The resultant echoes are processed to image the operation of the surgical device.

In some embodiments, a small (longitudinal), transverse, biplane, multiplane, dynamic phased, stereoscopic, and three-dimensional phased array ultrasound transducer is combined with a catheter delivery system. It is appreciated that this system incorporates not only tomographic, but also three-dimensional, stereoscopic, and virtual reality ultrasound environments. In a preferred embodiment, the device incorporates a 5 to 10 MHz phased array transducer with a (8 French conduit) delivery port. The delivery port serves as a means to deliver other catheters (i.e., ablation catheters, etc.), record pressure and sample blood. Within the core of the ultrasound catheter there is also a 0.035 inch port for wire insertion. The completed catheter device typically might require an 18 to 24 French sheath for venous entry.

The present invention might have numerous applications. One initial application might be the ablation of right heart conduction tracts. The proposed device would be ideal for ablation of right heart bypass tracts. The tricuspid valve and its annulus could be confidently mapped by direct ultrasound visualization. An electrophysiologic catheter or ablation catheter could be passed through the port contained in the catheter. The catheter could be manipulated to its destination by use of a deflection wire disposed in the guide wire port. Precise mapping and intervention can then be carried out under direct ultrasound visualization.

Other applications include ultrasound guided myocardial biopsy, surgical implantation and/or removal of devices under ultrasound control, and transvascular diagnosis of perivascular and organ pathology.

The present invention provides an intravascular ultrasound catheter capable of catheter-based intervention while under visual observation. Avoidance of major surgical procedures in conjunction with precision catheter intervention is a substantial improvement over present patient care.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

Brief Description of the Drawings

A better understanding of the construction and operational characteristics of a preferred embodiment(s) can be realized from a reading of the following detailed description, especially in light of the accompanying drawings in which like reference numerals in the several views generally refer to corresponding parts.

FIG. 7A shows a partial perspective and cross-sectional view of a variation of the second alternate embodiment of the catheter shown in FIG. 6A;

FIG. 7B shows a view of the distal end of the embodiment of the catheter shown in FIG. 7A;

FIG. 8A shows a partial perspective and cross-sectional view of a third alternate embodiment of a catheter in accordance with the principles of the present invention;

FIG. 8B shows a view of the distal end of the catheter shown in FIG. 8A;

FIG. 8C shows a view of the distal end of the catheter shown in FIG. 8A having an alternatively shaped secondary port;

FIG. 9A shows partial perspective and cross-sectional view of a fourth alternate embodiment of a catheter in accordance with the principles of the present invention; and FIG. 9B shows a view of the distal end of the catheter shown in FIG. 9A.

DETAILED DESCRIPTION OF A PREFERRED EMBODIMENT

Figure 1:
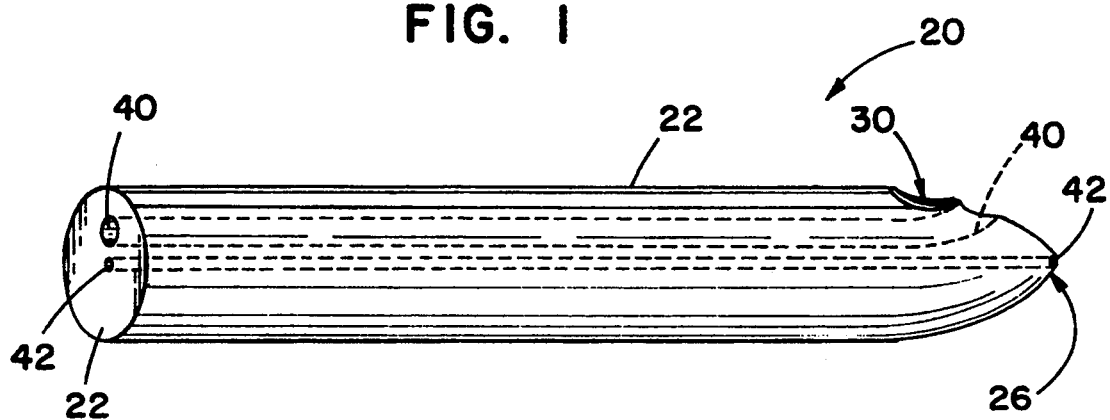
FIG. 1 is a partial perspective view of an embodiment of a catheter in accordance with the principles of the present invention.
Figure 2:
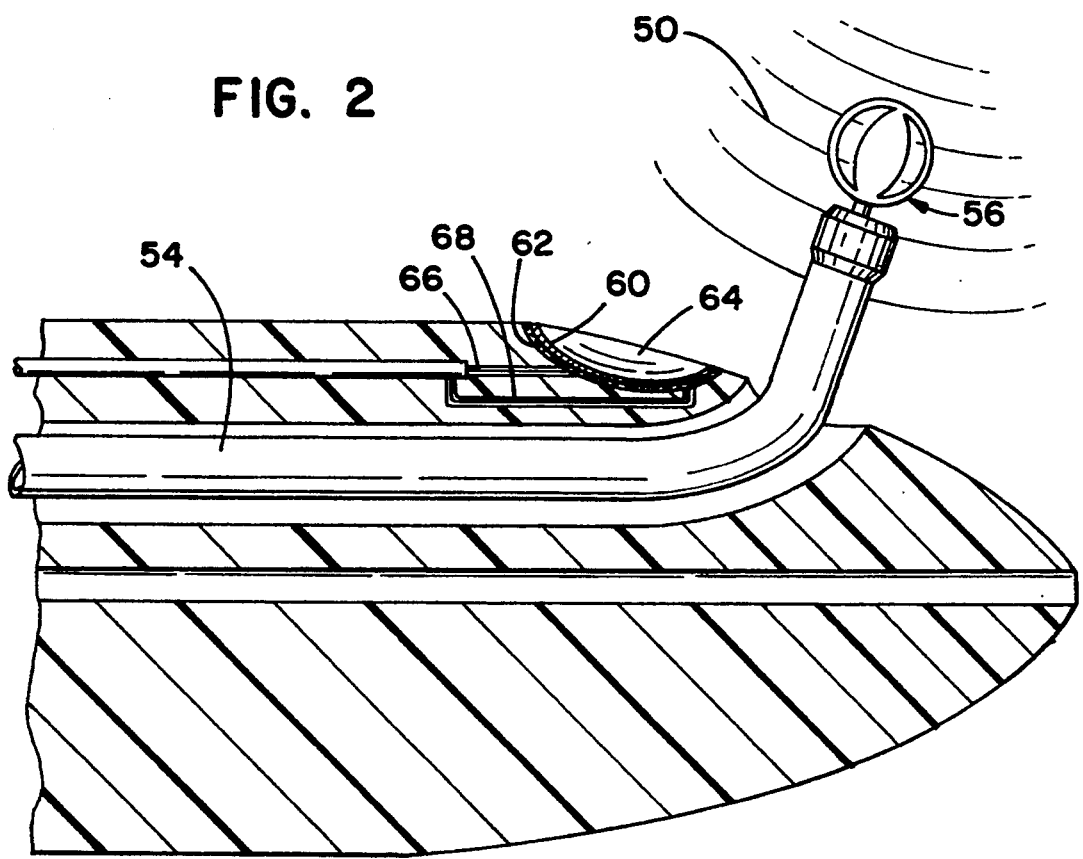
FIG. 2 is a block diagram in part and sectional diagram in part illustrating an embodiment of a system utilizing the catheter shown in FIG. 1.
Figure 3:
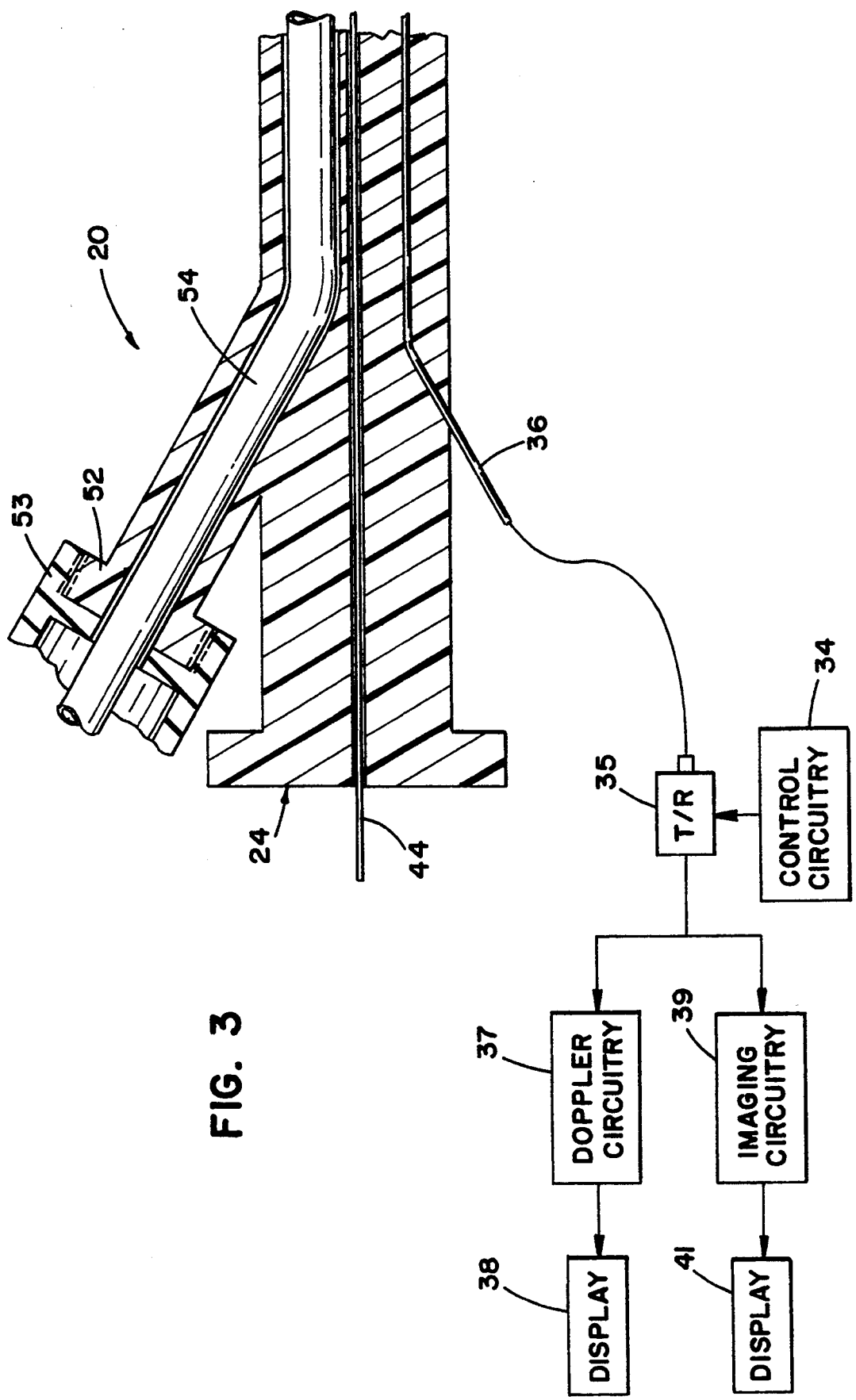
FIG. 3 is an enlarged cross-sectional view taken proximate the proximal end of the catheter shown in FIG. 1.

Referring now to FIGS. 1–3, there is, generally illustrated by reference numeral 20, a catheter in accordance with the principles of the present invention. As shown, catheter 20 includes an elongated flexible or rigid plastic tubular catheter body 22 having a proximal end 24 and a distal end 26. Catheter 20 includes proximate its longitudinal distal end 26 a phased array ultrasonic transducer 30 which is used to transmit ultrasound and receive resultant echoes so as to provide a field of view within which flow rates can be measured and features imaged. It is appreciated that the other types of ultrasonic transducers can be used in the present invention, such as any mechanical types, or any dynamic array types, or any offset stereoscopic imaging types, or any multidimensional imaging types incorporated into a virtual reality environment for underblood operation, etc. An electrical conductor 32 is disposed in the catheter body 22 for electrically connecting transducer 30 to control circuitry 34 external of catheter body 22. An access port 40 is disposed in catheter body 22 and extends from proximate the proximal end 24 of catheter body 22 to proximate the distal end 26 of catheter body 22. Access port 40 is configured to receive a therapeutic device, such as a catheter, medication, sensors, etc., so as to enable such items to be delivered via access port 40 to distal end 26 of catheter body 22 for operation within the ultrasonic transducer field of view. Such items might be used for intervention; e.g., ablation catheter, surgical device, etc., monitoring blood pressure, sampling blood, etc. A guide wire access port 42 is also disposed within catheter body 22 and extends from proximate proximal end 24 of the catheter body 22 to proximate distal end 26 of catheter body 22 for receiving a guide wire 44.

In the preferred embodiment of the present invention, the ultrasonic transducer preferably has a frequency of 5 to 20 megahertz (MHz) and more preferably a frequency of 7 to 10 MHz. Intracardiac imaging in an adult will require image penetration of up to 2 to 10 centimeters (cm). In the preferred embodiment, catheter body 22 preferably has a diameter of 4 to 24 French [one French divided by Pi equals one millimeter (mm)] and, more preferably, a diameter of 6 to 12 French. In the preferred embodiment, access port 40 has a diameter of 7 to 8 French and guide wire port 42 has a diameter of 0.025 to 0.038 inches.

As generally illustrated in FIG. 3, catheter 20 of the present invention can be utilized in a medical system including the appropriate control circuitry 34 for controlling operation of the ultrasonic transducer. As illustrated in FIG. 3, control circuitry 34 is electrically interconnected to transceiver circuitry 35 (T/R) for receiving and transmitting signals via a cable 36 to ultrasonic transducer 30. In turn, transceiver circuitry 35 is electrically interconnected to Doppler circuitry 37 and an appropriate display device 38 for displaying hemodynamics or blood flow. In addition, transceiver circuitry 35 is electrically interconnected to suitable imaging circuitry 39 which is interconnected to a display 41 for displaying images.

During operation, control circuitry 34 might be designed to cause ultrasonic transducer 30 to vibrate so as to cause an appropriate ultrasound wave to project from proximate the distal end 26 of catheter body 22. The ultrasound wave, represented by lines 50 in FIG. 2, will propagate through the blood surrounding distal end 26 and a portion of the body structure. A portion of the ultrasound wave so transmitted will be reflected back from both the moving red blood cells and the like and the body structures to impinge upon transducer 30. An electrical signal is thereby generated and transmitted by the cable 36 to the input of transceiver 35. A signal might then be transmitted to Doppler circuitry 37 which will include conventional amplifying and filtering circuitry commonly used in Doppler flow metering equipment. Doppler circuitry 37 will analyze the Doppler shift between the transmitted frequency and the receive frequency to thereby derive an output proportional to flow rate. This output may then be conveniently displayed at display 38 which might be a conventional display terminal. Accordingly, the user will be able to obtain a readout of blood flow rates or hemodynamic information.

In order to obtain imaging information, control circuitry 34 will likewise trigger ultrasonic transducer 30 via transceiver 35 to vibrate and produce an ultrasound wave. Once again, a portion of the wave or energy will be reflected back to ultrasonic transducer 30 by the body features. A corresponding signal will then be sent by cable 36 to transceiver circuitry 35. A corresponding signal is then sent to the imaging circuitry 39 which will analyze the incoming signal to provide, at display 41, which also might be a conventional display apparatus, an image of the body features.

This imaging can occur while a therapeutic or surgical device is being used at distal end 26 of catheter 20 within the field of view provided by ultrasonic transducer 30. Accordingly, the user will be able to monitor his/her actions and the result thereof.

As illustrated in FIG. 3, catheter body 22 might include proximate its proximal end 24 a suitable mounting structure 52 to the access port 40. A therapeutic or surgical device structure 53 might be suitably attached to structure 52 by suitable means, e.g., threaded, etc. As illustrated, an elongated cable-like member 54 will extend along access port 40 and slightly beyond distal end 26 of catheter body 22 wherein an operative portion 56 of the surgical tool might be interconnected.

Figure 4A:
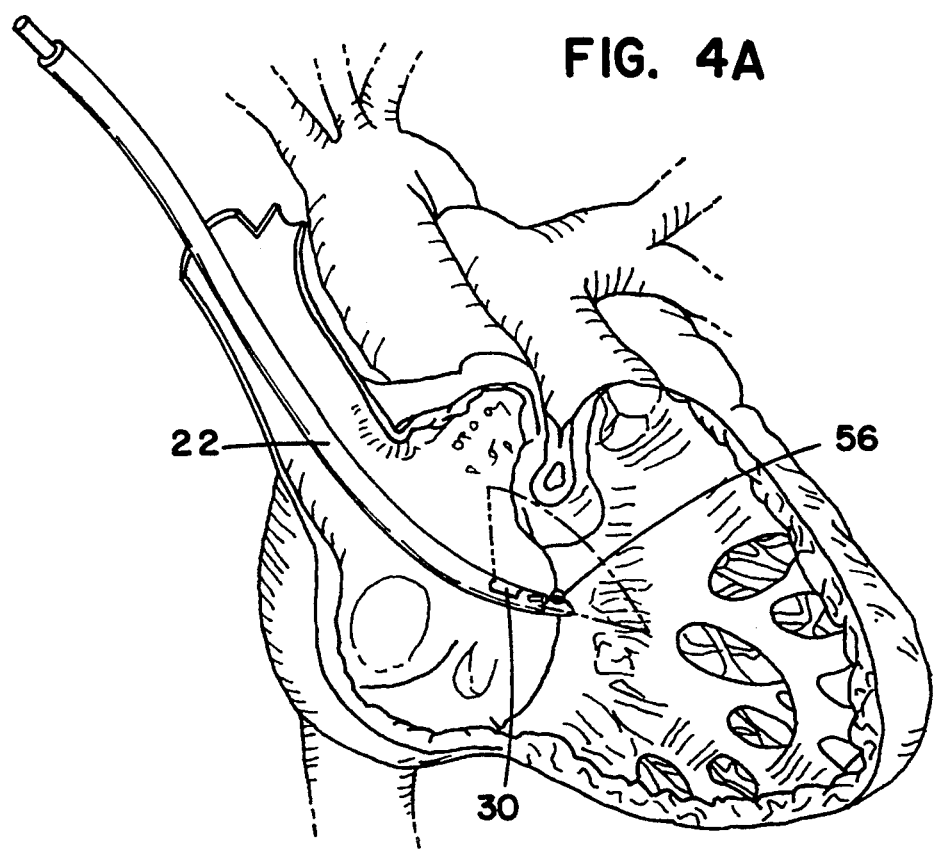
FIG. 4A is an illustration illustrating an application of a catheter in accordance with the principles of the present invention.
Figure 4B:
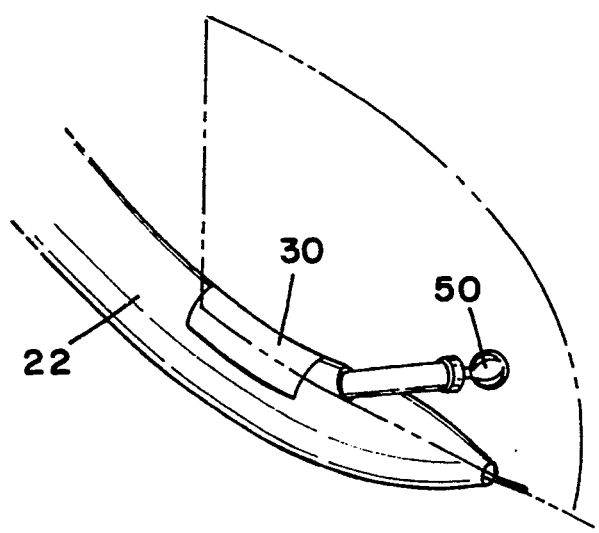
FIG. 4B is a partially enlarged illustration of the catheter shown in FIG. 4A.

Additional detail of distal end 26 of catheter body 22 is illustrated in FIGS. 4A and 4B. As illustrated in FIGS. 4A and 4B, ultrasonic transducer 30 might include a piezo electric polymer, such as Polyvinylidenedifloride (PVDF) 60, which is bonded by an epoxy layer 62 to a depression 64 approximate distal end 26. Although some detail is provided with respect to an embodiment of an ultrasonic transducer which might be used, it will be appreciated that various types of transducers having various configurations and orientations might be utilized in keeping with the present invention.

As illustrated in FIGS. 4A and 4B, the operational portion 56 of the therapeutic device is illustrated as generally being capable of operation in the field of view of ultrasonic transducer 30. Accordingly, it is possible for the user to monitor operation of the therapeutic device by use of the ultrasonic transducer. Moreover, it is possible for the user to monitor the features of the body within the field of view before, during and after interventional activity. It is appreciated that the other types of ultrasonic transducers can be used in the present invention, such as any mechanical types, or any dynamic array types, or any offset stereoscopic imaging types, or any multidimensional imaging types incorporated into a virtual reality environment for underblood operation, etc., so that all forms of field of views, such as 1) tomographic (slices), 2) stereoscopic, 3) three-dimensional, 4) virtual reality (multidimensional) can be provided in the present invention. In addition, it is appreciated that the orientations of the scan array on the catheter can include side-view, end-view, multiview (two or more views that are movable or imminently directional transducer referred to in the literature as "omnidirectional"), etc.

Figure 5A:
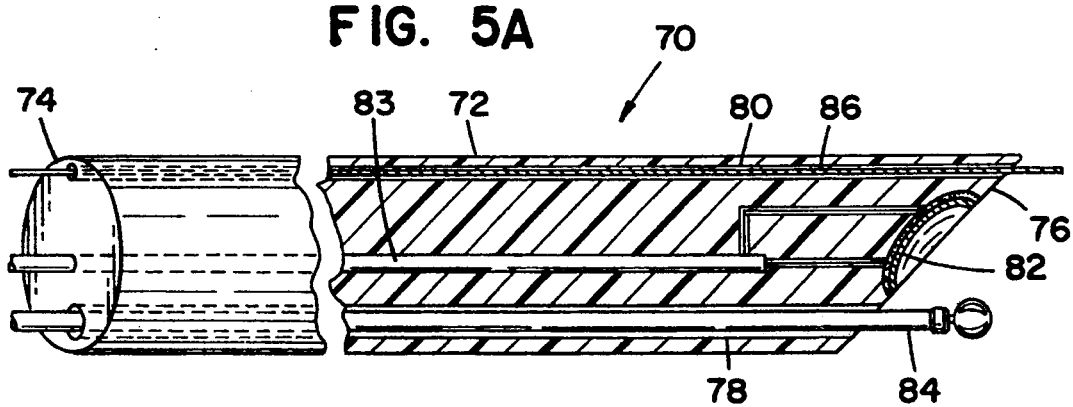
FIG. 5A shows a partial perspective and cross-sectional view of a first alternate embodiment of a catheter in accordance with the principles of the present invention.

FIG. 5A shows a partial cross-sectional view of a first alternative embodiment 70 of the catheter apparatus. The catheter apparatus has an elongated flexible or rigid body 72 having a longitudinal axis and a proximal end 74 and a distal end 76. Disposed proximate a second side of body 72 is a port 78 extending through body 72 from proximate proximal end 74 to proximate distal end 76 of body 72. Port 78 is for receiving and delivering to distal end 76 of body 72 a working tool 84. Working tool 84 shown in the Figures is illustrative only, others types of tools now known or later developed may also be delivered to distal end 76 through port 78. Proximate a first side of body 72 is a guide wire port 80 extending through body 72 from proximate proximal end 74 to proximate distal end 76. Shown in guide port 80 is a guide wire 86.

Distal end 76 is disposed at an oblique angle to the longitudinal axis of body 72, the first side of body 72 extending further in the direction of the distal end than the second side of body 72. An ultrasonic transducer 82, having a first side and a second side, is disposed at an oblique angle to the longitudinal axis of body 72 approximately corresponding to the oblique angle of distal end 76 of body 72. The first side of ultrasonic transducer 82 is disposed proximate the first side of body 72 and the second side of transducer 82 is disposed proximate the second side of body 72. Extending from transducer 82 to proximate proximal end 74 of body 72 is an electrical conductor 83 connecting transducer 82 to control circuitry external of catheter 70, as described with respect to catheter 20 above. Having transducer 82 disposed on an oblique angle toward port 78 allows for easy visualization of tools, such as tool 84, extending beyond distal end 76 of body 72.

Figure 5B:
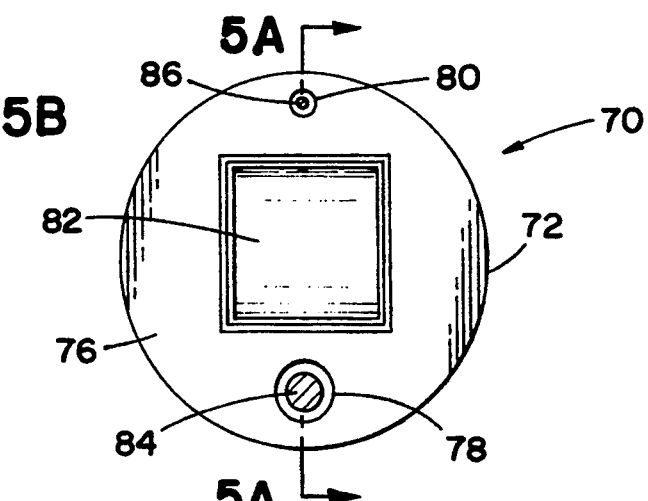
FIG. 5B shows a view of the distal end of the embodiment of the catheter shown in FIG. 5A.

FIG. 5B shows a view of distal end 76 of body 72, showing guide wire port means 80, transducer 82, and port means 78.

Figure 6A:
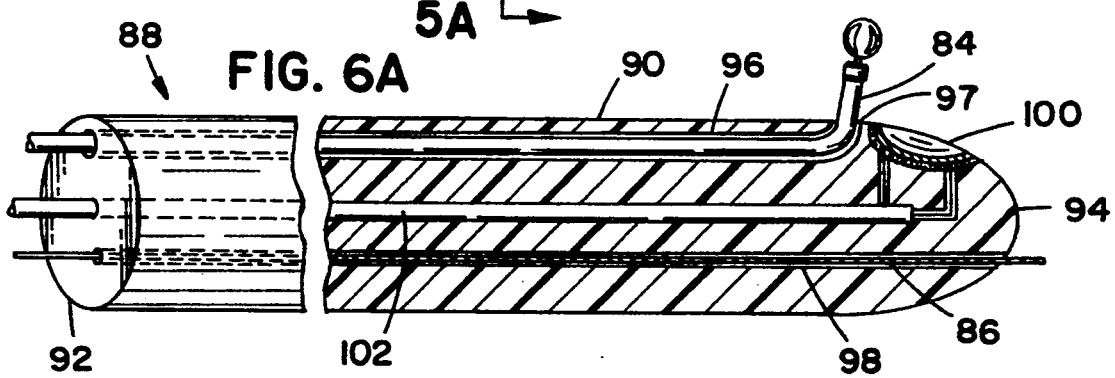
FIG. 6A shows a partial perspective and cross-sectional view of a second alternate embodiment of a catheter in accordance with the principles of the present invention.

FIG. 6A shows a partial cross-sectional view of a second alternative embodiment of the catheter in accordance with the present invention, generally referred to as 88. Like first alternative embodiment 70, catheter 88 has an elongated flexible or rigid body 90 having a proximal end 92 and a distal end 94. Catheter 88 also has a port 96 extending through body 90 from proximate proximal end 92 to proximate distal end 94. Port 96 has a distal end 97 proximal distal end 94 of body 90. Distal end 97 of port 96 exits body 90 at an acute angle to a first side of body 90 toward distal end 94. Port 96 is for receiving and delivering to distal end 94 a working tool, such as working tool 84. Catheter 88 also has a guide wire port 98 extending through body 90 from proximate proximal end 92 to proximate distal end 94. Guide wire port 98 is for receiving a guide wire 86.

Also shown in FIG. 6A is a transducer 100 disposed to a first side of body 90 between distal end 94 and distal end 97 of port 96. Extending from transducer 100 to proximate proximal end 92 of body 90 is an electrical conductor 102 disposed in the catheter body 90 for electrically connecting transducer 100 to control circuitry external of the catheter. With transducer 100 disposed to the first side of body 90 and distal end 97 of port 96 exiting body 90 at an acute angle relative to the first side of body 90 toward distal end 94, working tools extending from distal end 97 of port 96 will be within the field of view of transducer 100.

Figure 6B:
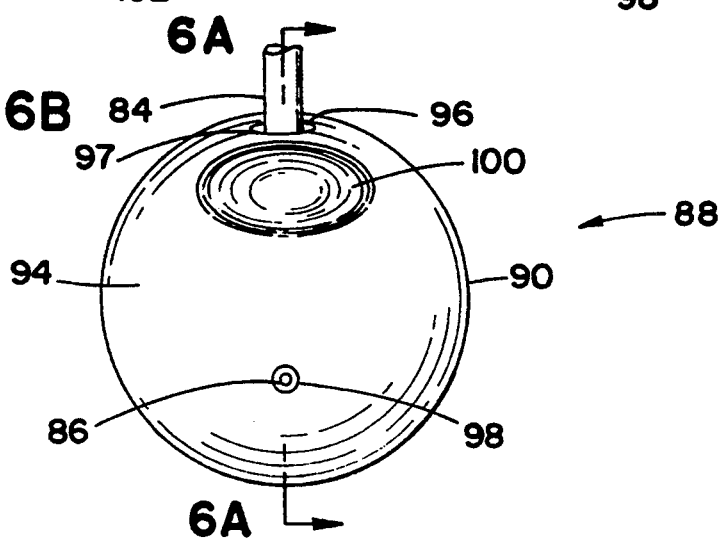
FIG. 6B shows a view of the distal end of the catheter shown in FIG. 6A.

FIG. 6B shows a view of distal end 94 of catheter 88, as shown in FIG. 6A.

FIG. 7A shows second alternative embodiment 88, as shown in FIG. 6A, except instead of having a guide wire port 98, this variation of the second alternative embodiment 88 has a deflection wire guidance system 106 for manipulating distal end 94. FIG. 7B shows a view of distal end 94 of the catheter shown in FIG. 7A.

FIG. 8A shows a third alternative embodiment 110 of the catheter in accordance with the present invention. Third alternative embodiment 110 has a body 112 having a distal end 114 and proximal end 116. Disposed proximate a first side of body 112 is a primary port 118 extending through body 112 from proximate proximal end 116 to proximate distal end 114. Primary port 118 has a distal end 119 proximate distal end 114 of body 112. Oppositely disposed from primary port 118, proximate a second side of body 112 is a secondary port 120 extending through body 112 from proximate proximal end 116 to proximate distal end 114. Secondary port 120 has a distal end 121 proximate distal end 114 of body 112.

Mounted proximate distal end 114 of body 112 is a transducer 122. Extending from transducer 122 through body 112 to proximate proximal end 116 is an electrical conductor for electrically connecting the transducer 122 to control circuitry external of the catheter. Transducer 122 is disposed between distal ends of primary and secondary ports 119 and 121, respectively. With working ports 118 and 120 oppositely disposed on either side of transducer 122, it is possible to conduct two simultaneous applications, such as holding an object wit a first tool disposed through one port and operating on the object held by the first tool with a second tool disposed through the other port. A typical working tool 123 and working tool 84 are shown disposed with ports 118 and 120.

Although third alternative embodiment 110 does not include a guide wire port means, a guide wire could be used in primary port 118 or secondary port 120 to initially position catheter 110. Then the guide wire could be retracted from port 118 or 120 and a working tool introduced. FIG. 8B shows a view of distal end 114 of catheter 110.

FIG. 8C shows a view of a distal end 124 of a catheter 126 substantially like catheter 110 shown in FIG. 8A and FIG. 8B, except that catheter 126 has a primary port 128 having an arc-like shaped cross-section, rather than a circular shaped cross-section. Although a circular cross-section has been shown in the Figures for the various ports described herein, the size and shape of the ports can be varied without departing from the principals of the present invention.

FIG. 9A shows a fourth alternative embodiment 130 of the catheter of the present invention. Catheter 130 is similar to catheter 70 shown in FIG. 5A and FIG. 5B, except that a plurality of ports 132 are disposed proximate a second side of flexible body 131, rather than one port 78, as shown in FIG. 5A. With a plurality of ports, it is possible, for example, to use a therapeutic tool through one port while simultaneously suctioning and removing debris through another port; or a therapeutic tool can be used through one port while simultaneously electrophysiologically monitoring, suctioning and/or biopsying through a second port, third or fourth port.

The use of the catheter of the present invention is described with respect to the preferred embodiment 20. It is understood that the use of alternative embodiments 70, 88, 110, 126 and 130 is analogous. In use, the user would insert flexible catheter body 22 into the body via the appropriate vascular access to the desired location in the body, such as selected venous locations, heart chamber, etc. In one approach, a guide wire might be first inserted into place and then the catheter body fed along the guide wire. The user might then insert a surgical device into the body through access port 40 and feed the surgical device to proximate distal end 26 of catheter body 22. Prior to, during and after operation of the surgical device, the user might obtain both hemodynamic measurements and images from the ultrasonic transducer field of view. By operation of the surgical device within the field of view of transducer 40, the user can monitor operation of the surgical device at all times.

I. DETAILED FEATURES OF THE DISCLOSED CATHETERS

A. Frequency Agility Ultrasound Frequency

Frequency Agility refers to the ability of a transducer to send and receive at various frequencies, most commonly 3, 5, and 7 MHz. It is also appreciated that a single frequency from a single transducer device can be sent and received. In general, higher frequencies are used to image fine detail of more proximal or closely related objects while lower frequency transducers scan more remote objects with less detail. The proposed device optimally uses a 5 to 20 mHz transducer with the most optimally applied frequency of 7 to 10 mHz. The lower frequency used in the UIHC reflects the need to image larger objects such as the cardiac septa, valves, and extravascular anatomy.

B. Catheter size

Catheter diameters will generally be larger than intravascular catheters and will range 4 to 24 French with the optimal catheter diameter 6 to 12 French (French size=French divided by Pi plus millimeter diameter).

C. Intervention

One primary function of this catheter system is to guide the logical and safe use of various a) ablation, b) laser, c) cutting, d) occluding, e) etc., catheter-based interventional cardiovascular tools. The invention has the access port through which other technologies (devices) can be passed. Once the interventional tool exits the catheter tip, it can be directed repeatedly and selectively to specific site for controlled intervention.

D. Imaging

The invention is also an imaging system capable of visualizing intracardiac, intravascular, and extravascular structures. Because the transducer frequencies utilized are usually lower than intravascular systems, the catheter 20 can see multiple cardiac cavities and visualize structures outside the vascular system. The imaging capability is basically two-fold: 1) diagnostic and 2) application.

1. Diagnostic imaging: The catheter 20 can effectively perform diagnostic intracardiac and transvascular imaging. This application will more than likely be performed just prior to an interventional application. The intervention then will follow using the same catheter system and its unique delivery capability. Some examples of diagnostic imaging include 1) accurate visualization and measurement of an intracardiac defect, 2) characterization of valve orifice, 3) localization of a tumor and its connections, 4) etc. Extravascular diagnoses would include 1) visualize pancreatic mass/pathology, 2) retroperitoneal pathology, 3) intracranial imaging, 4) recognition of perivascular pathology, and 5) etc.

2. Application imaging refers to the use of the catheter and its imaging capability to deliver and then apply another technology such as 1) occlusion device for closure of a septal defect, 2) ablation catheters for treatment of bypass tracts, 3) creation of a defect such as that with the blade septostomy catheter or laser-based catheter system, and 4) directing of valvuloplasty, etc. By direct imaging of an application, such as ablation, the procedure will be able to be performed more safely and repeatedly, and the result can be better assessed.

E. Hemodynamics

The catheter 20 is a truly combined ultrasound Doppler and conventional hemodynamic catheter. There are Doppler catheters, and there are catheters capable of imaging and measuring hemodynamic pressure. However, the catheter 20 is capable of Doppler hemodynamics (continuous and pulsed-wave Doppler) as well as high-fidelity hemodynamic pressure recording while simultaneously imaging the heart and blood vessel. The catheter 20 provides a combination of imaging, hemodynamic, and interventional delivery catheter.

II. ANALOGY WITH OTHER EXISTING THERAPEUTIC TECHNOLOGIES

Like interventional peritoneoscopy, intracardiac ultrasound is capable of 1) imaging, 2) delivering a therapeutic device, and 3) obtaining simultaneous hemodynamics which can be used to develop less invasive cardiac surgical techniques. This simultaneous use of one or more devices within the heart or vascular tree opens up the potential to develop less invasive surgical therapies. Examples would include 1) removal of a cardiac tumor by visually grasping the tumor with one device and visually cutting its attachment with a second device, thus allowing less invasive extraction of intracardiac mass lesions, 2) visually placing an electrophysiologic catheter on a bypass tract and then with direct ultrasound visualization ablate the underlying tract with the second device, 3) visually performing laser surgery such as creating an intra-atrial defect, vaporization of obstructing thrombus such as is seen in pseudointimal occlusion of conduits, 4) visually removing a foreign body from the heart or vascular tree, and 5) directing intravascular surgery from within a blood vessel or monitoring concomitant hemodynamic changes.

III. SELECTED APPLICATIONS INCLUDE THE FOLLOWING

A. Radio frequency ablation

Presently a bypass tract is localized by an electrophysiologic study which systematically maps the atrioventricular valve annulus. Positioning of the ablation catheter is determined by x-ray fluoroscopy and certain electrical measurements which relate the distance of the ablation catheter from a reference catheter. The catheter 20 will allow an operator to map the atrioventricular valve under direct ultrasound visualization. Thus, increased accuracy of catheter placement, precision of the applied therapy, and immediate assessment of outcome would result.

The above ablation technique would be particularly applicable for right-sided bypass tracts (in and around the tricuspid valve annulus). This would be accomplished by placement of the catheter 20 through the superior vena cava above the tricuspid annulus.

For left-sided bypass tracts, the catheter 20 could be placed across the atrial septum under direct ultrasound visualization. The mitral annulus could thus be mapped directly and the localized bypass tract precisely ablated under visual ultrasonic and hemodynamic direction. Complications such as valve perforation, multiple imprecise applications of ablation energy, and inadvertent ablation of normal conduction tissue would be substantially reduced.

Ablation of bypass tracts would be an ideal utilization of the proposed ultrasonic interventional catheter system.

B. Cardiac Biopsy

In the era of safe cardiac biopsy, there is a need for precision biopsy. Ultrasound direction of the biopsy device to an intracardiac tumor, avoidance of scar, and selective biopsy of suspect tissue are feasible with the catheter 20 device. One of the more frequently life-threatening complications in the cardiac catheterization laboratory is catheter perforation of the heart. Such complications most commonly accompany cardiac biopsy, electrophysiologic catheter manipulation, and valvuloplasty. Use of an intracardiac ultrasound imaging, hemodynamics, and delivery catheter should substantially increase or improve safety of these procedures.

C. Transvascular Diagnoses

The catheter 20 will allow visualization of perivascular and extravascular pathology. Transvascular or transorgan imaging and localization of pathology out of the immediate vascular tree will result in a substantial step forward in the diagnosis and possible treatment of difficult to reach pathology. The catheter 20 cannot only diagnose but guide a biopsy needle and therapeutic device to an extravascular lesion in question. The retroperitoneum, mediastinum, and basal cerebrovascular pathology are logical areas of interest. Accurate characterization of various pathologies will be more feasible. Every organ has its own vascular system, and the proposed ultrasound transvascular system is an ideal tool to assess difficult to reach areas of the body. The vascular system is a conduit to each organ, and the catheter 20 can be delivered to each organ. Characterization of the underlying parenchyma and possible transvascular biopsy or treatment will ultimately be developed.

D. Ultrasound Manipulation of Therapeutic Devices within the Heart and Blood Vessels The catheter 20 opens the potential not only to visualize but to directly intervene with the same catheter system. There are numerous intraoperative catheter-based systems which to date use conventional x-ray to accomplish their goal of placement and application of a specified therapy. There is a need for a device which can more precisely guide such catheter-based systems. It is too expensive and technically impractical to incorporate ultrasound into every catheter-based technology. The catheter 20 has all the prerequisites of an ideal imaging and interventional instrument and has the ability to 1) image, 2) obtain hemodynamics by multiple means (pressure dynamics and Doppler, 3) function as a diagnostic as well as therapeutic device, and 4) accommodate other unique technologies which would enhance the application of both systems.

E. General Applications

It is anticipated that intravascular, transvascular, and intracardiac devices could be delivered through the port means described above within or about the heart and blood vessels of the body. The catheters described above, however, could also be used in any echogenic tissue, such as liver, parenchyma, bile ducts, ureters, urinary bladder, and intracranial—i.e., any place in the body which is echogenic which would allow passage of a catheter for either diagnostic or therapeutic applications using ultrasound visualization.

F. Expanding Applications of Technologies

The catheter 20 is a new and exciting innovation to invasive medicine. There are multiple other and yet-to-be-determined applications. However, the new concept described opens the potential development of less expensive, more precise, and safe intravascular and transvascular diagnostic and surgical devices.

IV. Summary

The catheter 20 is very much different from any conventional ultrasound catheter-based system. The catheter 20 incorporates image and hemodynamic capability as well as the ability to deliver other diverse technologies to specified sites within the cardiovascular system (heart and blood vessels). The catheter 20 is seen as an ideal diagnostic and therapeutic tool for future development. The proposed applications foster greater preciseness, adaptability, and safety. Ultrasound permits visualization from within blood-filled spaces as well as through blood-filled spaces into other water- or fluid-filled tissue. The catheter 20 will evolve into the ultimate interventional system.

FIG. 4A is an illustration showing one potential use of the ultrasound imaging and hemodynamic catheter (UIHC). In this particular example, the UIHC is advanced from the superior vena cava to the tricuspid valve annulus. Simultaneously visualized in the annulus, electrophysiologic and ultimately and ablation procedure are performed. The ability to directly visualize and direct therapeutic catheter devices highlights only one of the many applications of the UIHC.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus, comprising:
   an elongated body having proximal and distal ends and first and second sides, wherein the first side extends further in the direction of the distal end of the catheter body than the second side;
   a port disposed in the catheter body proximate the second side of the catheter body, the port extending from proximate the proximal end of the catheter body to proximate the distal end of the catheter body for receiving a therapeutic device whereby a therapeutic device can be delivered to proximate the distal end of the catheter;
   an ultrasonic transducer having a first side and a second side, the ultrasonic transducer being mounted proximate the distal end of the catheter body and being disposed between the port and the first side of the catheter body with the first side of the ultrasonic transducer being proximate the first side of the body and the second side of the transducer being proximate the second side of the body, so that the transducer is tilted toward the port to transmit ultrasound and receive resultant echoes to provide a field of view within which flow rates can be measured and features imaged including the therapeutic device delivered to proximate the distal end of the catheter through the port; and
   an electrical conductor disposed in the catheter body for electrically connecting the transducer to control circuitry external of the catheter.

2. The catheter apparatus, in accordance with claim 1, further comprising a guide wire port disposed in the catheter body proximate the first side of the catheter body, the guide wire port extending from proximate the proximal end of the catheter body to proximate the distal end of the catheter body for receiving a guide wire.

3. A catheter apparatus, comprising:
   an elongated body having proximal and distal ends, and a first side;
   a port having a distal end, the port being disposed in the catheter body and extending from proximate the proximal end of the catheter body to proximate the distal end of the catheter body, the distal end of the port exiting the catheter body proximate the first side and the distal end of the catheter body at an acute angle to the first side of the catheter body, whereby a therapeutic device can be delivered to proximate the distal end of the catheter;

an ultrasonic transducer mounted on the first side of the catheter body between the distal end of the port and the distal end of the catheter body to transmit ultrasound and receive resultant echoes so as to provide a field of view within which flow rates can be measured and features imaged including the therapeutic device delivered to proximate the distal end of the catheter through the port; and an electrical conductor disposed in the catheter body for electrically connecting the transducer to control circuitry external of the catheter.

4. The catheter apparatus in accordance with claim 3, further comprising a guide wire port disposed in the catheter body and extending from proximate the proximal end of the catheter body to proximate the distal end of the catheter body for receiving a guide wire.

5. The catheter in accordance with claim 3, further comprising a deflection wire guidance system.

6. A catheter apparatus, comprising:

an elongated body having a first side and a second side, and proximal and distal ends;

a primary port disposed proximate the first side of the catheter body and extending from proximate the proximal end of the catheter body to proximate the distal end of the catheter body for receiving a first therapeutic device whereby the first therapeutic device can be delivered to proximate the distal end of the catheter;

secondary port disposed proximate the second side of the catheter body and extending from proximate the proximal end of the catheter body to proximate the distal end of the catheter body for receiving a second therapeutic device whereby the second therapeutic device can be delivered to proximate the distal end of the catheter;

an ultrasonic transducer mounted between the primary port and the secondary port and proximate the distal end of the catheter body to transmit ultrasound and receive resultant echoes to provide a field of view within which flow rates can be measured and features imaged including the first and second therapeutic devices delivered to proximate the distal end of the catheter through the port, an operational end of each of the first and second therapeutic devices projecting from proximate the distal end of the catheter body into the field of view so as to allow visualization of the first and second therapeutic devices during their operation; and an electrical conductor disposed in the catheter body for electrically connecting the transducer to control circuitry external of the catheter.

7. A catheter apparatus, comprising:

an elongated body having proximal and distal ends and a first side and a second side, wherein the first side extends further in the direction of the distal end of the catheter body than the second side;

a plurality of ports disposed in the catheter body proximate the second side of the catheter body and extending from proximate the proximal end of the catheter body to proximate the distal end of the catheter body for receiving at least one therapeutic device whereby at least one therapeutic device can be delivered to proximate the distal end of the catheter;

an ultrasonic transducer having a first side and a second side, the ultrasonic transducer being mounted proximate the distal end of the catheter body, the transducer being disposed between the plurality of ports and the first side of the catheter body with the first side of the transducer proximate the first side of the catheter body and the second side of the transducer being proximate the second side of the catheter body, so that the transducer is tilted toward the plurality of ports to transmit ultrasound and receive resultant echoes so as to provide a field of view within which flow rates can be measured and features imaged including at least one therapeutic device delivered to proximate the distal end of the catheter through the plurality of ports, an operational end of at least one therapeutic device projecting from proximate the distal end of the catheter body into the field of view so as to allow visualization of at least one therapeutic device during its operation; and an electrical conductor disposed in the catheter body for electrically connecting the transducer to control circuitry external of the catheter.

8. The catheter apparatus in accordance with claim 7, further comprising a guide wire port disposed in the catheter body proximate the first side of the catheter body, the guide wire port extending from proximate the proximal end of the catheter body to proximate the distal end of the catheter body for receiving a guide wire.

* * * * *

UNITED STATES PATENT AND TRADEMARK OFFICE
CERTIFICATE OF CORRECTION

PATENT NO. : 5,345,940

DATED : September 13, 1994

INVENTOR(S) : Seward et al.

It is certified that errors appear in the above-identified patent and that said Letters Patent is hereby corrected as shown below:

In Cover Page, under item [56] "References Cited, U.S. PATENT DOCUMENTS", please delete:

| | | | |
|---|---|---|---|
| 4,162,282 | 7/1979 | Fulwyler et al. | 264/9 |
| 4,310,505 | 1/1982 | Baldeschwieler et al. | 424/1 |
| 4,533,254 | 8/1985 | Cook et al. | 366/176 |
| 4,586,512 | 5/1986 | Do-huu et al. | 128/660 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman | 514/6 |
| 4,689,986 | 9/1987 | Carson et al. | 73/19 |
| 4,728,575 | 3/1988 | Gamble et al. | 428/402.2 |
| 4,728,578 | 3/1988 | Higgins et al. | 428/462 |
| 4,737,323 | 4/1988 | Martin et al. | 264/4.3 |
| 4,781,871 | 11/1988 | West, III et al. | 264/4.3 |
| 4,865,836 | 9/1989 | Long, Jr. | 424/5 |
| 4,893,624 | 1/1990 | Lele | 128/399 |
| 4,900,540 | 2/1990 | Ryan et al. | 424/9 |
| 4,921,706 | 4/1990 | Roberts et al. | 424/450 |

In Cover Page, page 1, under item [56] "FOREIGN PATENT DOCUMENTS", please delete:

| | | |
|---|---|---|
| 0361894 | 4/1990 | European Pat. Off. . |
| WO80/02365 | 11/1980 | PCT Int'l. Appl. . |
| WO82/01642 | 5/1982 | PCT Int'l. Appl. . |
| WO86/01103 | 2/1986 | PCT Int'l. Appl. . |

UNITED STATES PATENT AND TRADEMARK OFFICE
CERTIFICATE OF CORRECTION

PATENT NO. : 5,345,940

DATED : September 13, 1994

INVENTOR(S) : Seward et al.

It is certified that errors appear in the above-identified patent and that said Letters Patent is hereby corrected as shown below:

In Cover Page, page 1, under item [56] "OTHER PUBLICATIONS", please delete:

Cheng et al, *Investigative Radiology*, vol. 22, pp. 47-55 (1987).
Crowe et al., *Archives of Biochemistry and Biophysics*, vol. 242, pp. 240-247 (1985).
Crowe et al., *Archives of Biochemistry and Biophysics*, vol. 220, pp. 477-484 (1983).
Dorland's Illusrated Medical Dictionary, p. 946, 27th ed. (W. B. Saunders Company, Philadephia 1988).
Fukuda et al., *J. Am. Chem. Soc.*, vol. 108, pp. 2321-2327 (1986).
Hope et al., *Biochimica et Biophysica Acta*, vol. 812, pp. 55-65 (1985).

In Cover Page, page 2, under "OTHER PUBLICATIONS", please delete:

*Liposome Technology*, Gregoriadis, G., ed., vol. I, pp. 1-18, 29-35, 51-65 and 79-107 (CRC Press, Inc. Boca Raton, Fla. 1984).
Madden et al., *Chemistry and Physics of Lipids*, vol. 53, pp. 37-46 (1990).
Mayer et al., *Biochimica et Biophysica Acta*, vol. 858, pp. 161-168 (1986).
Mayhew et al., *Methods in Enzymology*, vol. 149, pp. 64-77 (1987).

UNITED STATES PATENT AND TRADEMARK OFFICE
CERTIFICATE OF CORRECTION

PATENT NO. : 5,345,940

DATED : September 13, 1994

INVENTOR(S) : Seward et al.

It is certified that errors appear in the above-identified patent and that said Letters Patent is hereby corrected as shown below:

In Cover Page, page 2, under "OTHER PUBLICATIONS", please delete:

Regen et al., *J. Am. Chem. Soc.*, vol. 102, pp. 6638-6640 (1980).
Sinkula et al., *J. Pharm. Sci.*, vol. 64, pp. 181-210 (1975).
Shiina et al., "Hyperthermiaby Low-frequency Synthesized Ultrasound", *IEEE Engineering*, pp. 879-880, vol. 2 (abstract).
McAvoy et al., *IEEE Engineering, Ultrasonics Symposium Proceedings*, vol. 2, pp. 677'1248 (abstract).

Signed and Sealed this

Twenty-fourth Day of October, 1995

Attest:

BRUCE LEHMAN

*Attesting Officer*                *Commissioner of Patents and Trademarks*